US008163967B2

(12) United States Patent
Senetar

(10) Patent No.: US 8,163,967 B2

(45) Date of Patent: Apr. 24, 2012

(54) OXYGENATE CONVERSION TO OLEFINS WITH ENHANCED CARBONYL RECOVERY

(75) Inventor: John J. Senetar, Des Plaines, IL (US)

(73) Assignee: UOP LLC, Des Plaines, IL (US)

(*) Notice: Subject to any disclaimer, the term of this patent is extended or adjusted under 35 U.S.C. 154(b) by 1251 days.

(21) Appl. No.: 11/315,881

(22) Filed: Dec. 22, 2005

(65) Prior Publication Data

US 2007/0203382 A1 Aug. 30, 2007

(51) Int. Cl.
*C07C 1/00* (2006.01)
*B01J 8/00* (2006.01)

(52) U.S. Cl. ........ 585/639; 585/314; 585/315; 585/324; 585/638; 585/640; 585/836; 585/856; 585/910

(58) Field of Classification Search .................. 585/640, 585/809, 314, 315, 324, 638, 639, 836, 856, 585/910; 210/634, 749; 422/190; 208/256, 208/263, 273

See application file for complete search history.

(56) References Cited

U.S. PATENT DOCUMENTS

| | | | | |
|---|---|---|---|---|
| 6,037,516 | A | 3/2000 | Morford et al. | 585/836 |
| 6,121,504 | A * | 9/2000 | Kuechler et al. | 585/640 |
| 6,459,009 | B1 | 10/2002 | Miller | 585/809 |
| 6,559,248 | B2 | 5/2003 | Hendriksen et al. | 526/77 |
| 6,764,602 | B2 | 7/2004 | Shutt et al. | 210/663 |
| 6,838,587 | B2 | 1/2005 | Lattner et al. | 585/807 |
| 7,288,692 | B2 * | 10/2007 | Kuechler et al. | 585/809 |
| 2004/0104181 | A1 | 6/2004 | Shiota et al. | 210/762 |
| 2004/0225171 | A1 * | 11/2004 | Lumgair et al. | 585/639 |
| 2004/0254416 | A1 | 12/2004 | Risch et al. | 585/824 |

FOREIGN PATENT DOCUMENTS

WO WO 03/020670 A1 3/2003

* cited by examiner

*Primary Examiner* — Prem C Singh

(74) *Attorney, Agent, or Firm* — Arthur E Gooding

(57) ABSTRACT

Improved processing of an oxygenate-containing feedstock involving increased or enhanced removal or recovery of carbonyls, particularly, acetaldehyde via either or both application of a more stringent stripping regime or addition of a sulfite-containing material.

15 Claims, 2 Drawing Sheets

OXYGENATE CONVERSION TO OLEFINS WITH ENHANCED CARBONYL RECOVERY

BACKGROUND OF THE INVENTION

This invention relates generally to the conversion of oxygenates to olefins and, more particularly, to light olefins with enhanced carbonyl and, in particular, acetaldehyde, removal or recovery.

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. A major source for these materials in present day refining is the steam cracking of petroleum feeds. For various reasons including geographical, economic, political and diminished supply considerations, the art has long sought a source other than petroleum for the massive quantities of raw materials that are needed to supply the demand for these light olefin materials.

The search for alternative materials for light olefin production has led to the use of oxygenates such as alcohols and, more particularly, to the use of methanol, ethanol, and higher alcohols or their derivatives such as dimethyl ether, diethyl ether, etc., for example. Molecular sieves such as microporous crystalline zeolite and non-zeolitic catalysts, particularly silicoaluminophosphates (SAPO), are known to promote the conversion of oxygenates to hydrocarbon mixtures, particularly hydrocarbon mixtures composed largely of light olefins.

Such processing of oxygenates to form light olefins is commonly referred to as a methanol-to-olefin (MTO) process, as methanol alone or together with other oxygenate materials such as dimethyl ether (DME) is typically an oxygenate material most commonly employed therein. Such processing typically produces or results in a range of olefin reaction products as well as unreacted oxygenates and other trace oxygenates. Typical or common MTO processing schemes include an oxygenate absorber whereby circulated water is used to absorb oxygenates, e.g., methanol and DME, from the light olefin product. This oxygenate-containing circulated water is subsequently stripped in an oxygenate stripper to recover methanol and DME, with such recovered materials ultimately recycled to the oxygenate conversion reactor. The dewatered oxygenate conversion product stream resulting from the oxygenate absorber is passed to a $CO_2$ removal zone wherein the dewatered oxygenate conversion product stream is contacted with caustic to remove carbon dioxide and produce a caustic treated reactor product stream such as for subsequent processing through an appropriate light olefins recovery system.

Carbonyls, such as acetaldehyde, are common trace oxygenates in the oxygenate conversion reactor effluent and will typically be absorbed in the circulated water. Acetaldehyde, however, is commonly only incompletely stripped in the following oxygenate stripper such that the circulated water may experience a build-up in acetaldehyde concentration. The build-up of acetaldehyde and other carbonyls in the circulated water may severely decrease the effectiveness of the oxygenate absorber for removing acetaldehyde and other carbonyls. Incomplete removal of acetaldehyde and carbonyls may result in contamination of the treated olefin products. Moreover, acetaldehyde is known to cause fouling in the caustic scrubber positioned downstream of the oxygenate absorber.

Aqueous bisulfite solutions are known to react with aldehydes and other carbonyls, preferably methyl substituted carbonyls, to form a bisulfite addition product. As long as unreacted bisulfite ion is present, the bisulfite addition product will form. Sulfite, bisulfite, and the bisulfite addition products are typically either nonvolatile or have a sufficiently low volatility so as to avoid the significant removal thereof upon stripping associated aqueous solutions.

Aldehydes in MTO effluent may, for example, include formaldehyde, acetaldehyde, propionaldehyde, butyraldehyde, and crotonaldehyde. These compounds may be in the MTO reactor feed, created as reaction side products, or formed in processing downstream of the reactor.

Aqueous sulfite solutions generally contain an equilibrium mixture of bisulfite and sulfite ions. As the pH of such solutions is lowered below 7.0, bisulfite becomes the predominate species. A pH below 7.0 is generally preferred so as to have sufficient bisulfite present to react with the carbonyls. A pH above 6.5 is generally preferred so as to minimize pitting of carbon steel equipment.

In view of the above, there is a need and a demand for improved processing and systems for the conversion of oxygenates to olefins and, more particularly, for such processing and systems such as to enhance the removal, recovery or separation of carbonyls such as acetaldehyde, such as to facilitate or otherwise improve downstream processing.

SUMMARY OF THE INVENTION

A general object of the invention is to provide or result in improved processing of an oxygenate-containing feedstock to light olefins.

A more specific objective of the invention is to overcome one or more of the problems described above.

The general object of the invention can be attained, at least in part, through a process for producing light olefins from an oxygenate-containing feedstock. In accordance with one preferred embodiment, such a process involves contacting the oxygenate-containing feedstock in an oxygenate conversion reactor with an oxygenate conversion catalyst and at reaction conditions effective to convert the oxygenate-containing feedstock to form an oxygenate conversion effluent stream comprising fuel gas hydrocarbons, light olefins, $C_{4+}$ hydrocarbons and remaining oxygenate materials including a quantity of carbonyls. At least a portion of such remaining oxygenate material, including at least a portion of the quantity of carbonyls, is absorbed in a quantity of water to form an oxygenate-rich water process stream. Oxygenate materials are subsequently at least partially stripped from the oxygenate-rich water process stream to form a recycle water stream. At least a portion of such stripped oxygenates can desirably be recycled back to the MTO reactor for further conversion processing. At least a portion of the recycle water stream water forms the quantity of water used to absorb at least a portion of the remaining oxygenate material. The process involves the quantity of water having been treated to contain less than 150 mol ppm of carbonyls.

In accordance with another preferred embodiment, such a process involves contacting the oxygenate-containing feedstock in an oxygenate conversion reactor with an oxygenate conversion catalyst and at reaction conditions effective to convert the oxygenate-containing feedstock to form an oxygenate conversion effluent stream comprising fuel gas hydrocarbons, light olefins, $C_{4+}$ hydrocarbons and remaining oxygenate materials including a quantity of acetaldehyde. At least a portion of such remaining oxygenate material, including at least a portion of the quantity of acetaldehyde, is absorbed in a quantity of water to form an oxygenate-rich water process stream. Oxygenate materials are subsequently at least partially stripped from the oxygenate-rich water process stream to form a recycle water stream. At least a portion of the recycle water stream water forms the quantity of water used to absorb at least a portion of the remaining oxygenate material. The process involves the quantity of water having been treated to contain less than 150 mol ppm of acetaldehyde.

The prior art generally fails to provide processing schemes and arrangements for the conversion of an oxygenate-containing feedstock to olefins, particularly light olefins and which processing is as effective and efficient as may be desired for the removal or recovery of carbonyls, particularly acetaldehyde, such as to improve or facilitate downstream processing.

In accordance with another embodiment there is provided a system for converting oxygenates to light olefins. The system includes a reactor for contacting an oxygenate-containing feedstream with catalyst and converting the oxygenate-containing feedstream to form an oxygenate conversion effluent stream comprising fuel gas hydrocarbons, light olefins, $C_{4+}$ hydrocarbons and remaining oxygenate materials including a quantity of acetaldehyde. An absorber is provided for absorbing at least a portion of the remaining oxygenate material in a quantity of water to form an oxygenate-rich water process stream and a stream of hydrocarbon product. A stripper is provided for stripping oxygenate material from the oxygenate-rich water process stream to form a recycle water stream containing less than 150 mol ppm acetaldehyde and such as may be utilized to absorb at least a portion of the remaining oxygenate material in the absorber. In accordance with one embodiment, the hydrocarbon product is treated to contain less than 110 mol ppm of acetaldehyde.

A system for converting oxygenates to light olefins in accordance with yet another embodiment also includes a reactor for contacting an oxygenate-containing feedstream with catalyst and converting the oxygenate-containing feedstream to form an oxygenate conversion effluent stream comprising fuel gas hydrocarbons, light olefins, $C_{4+}$ hydrocarbons and remaining oxygenate materials including a quantity of acetaldehyde. The system also includes an absorber for absorbing at least a portion of the remaining oxygenate material in a quantity of water to form an oxygenate-rich water process stream. A stripper is provided for stripping oxygenate material from the oxygenate-rich water process stream to form a water stream. The system further includes a treatment system for treating the water stream with a sulfite-containing material to form a treated water stream containing no more than 150 mol ppm acetaldehyde, with such treated water forming the quantity of water used to absorb at least a portion of the remaining oxygenate material in the absorber.

As used herein, references to "light olefins" are to be understood to generally refer to $C_2$ and $C_3$ olefins, i.e., ethylene and propylene, alone or in combination.

Other objects and advantages will be apparent to those skilled in the art from the following detailed description taken in conjunction with the appended claims and drawings.

DETAILED DESCRIPTION OF THE INVENTION

As described above, an oxygenate-containing feedstock can be converted to olefins and, more particularly, to light olefins via a catalytic reaction. The light olefins produced or resulting from such conversion can be recovered from the oxygenate conversion reactor effluent via a recovery system employing water. As described in greater detail below, water employed in such processing can desirably be recycled and further employed in the process after having been appropriately treated to reduce the relative amount of possible objectionable characters such as carbonyls, particularly acetaldehyde.

Figure 1:
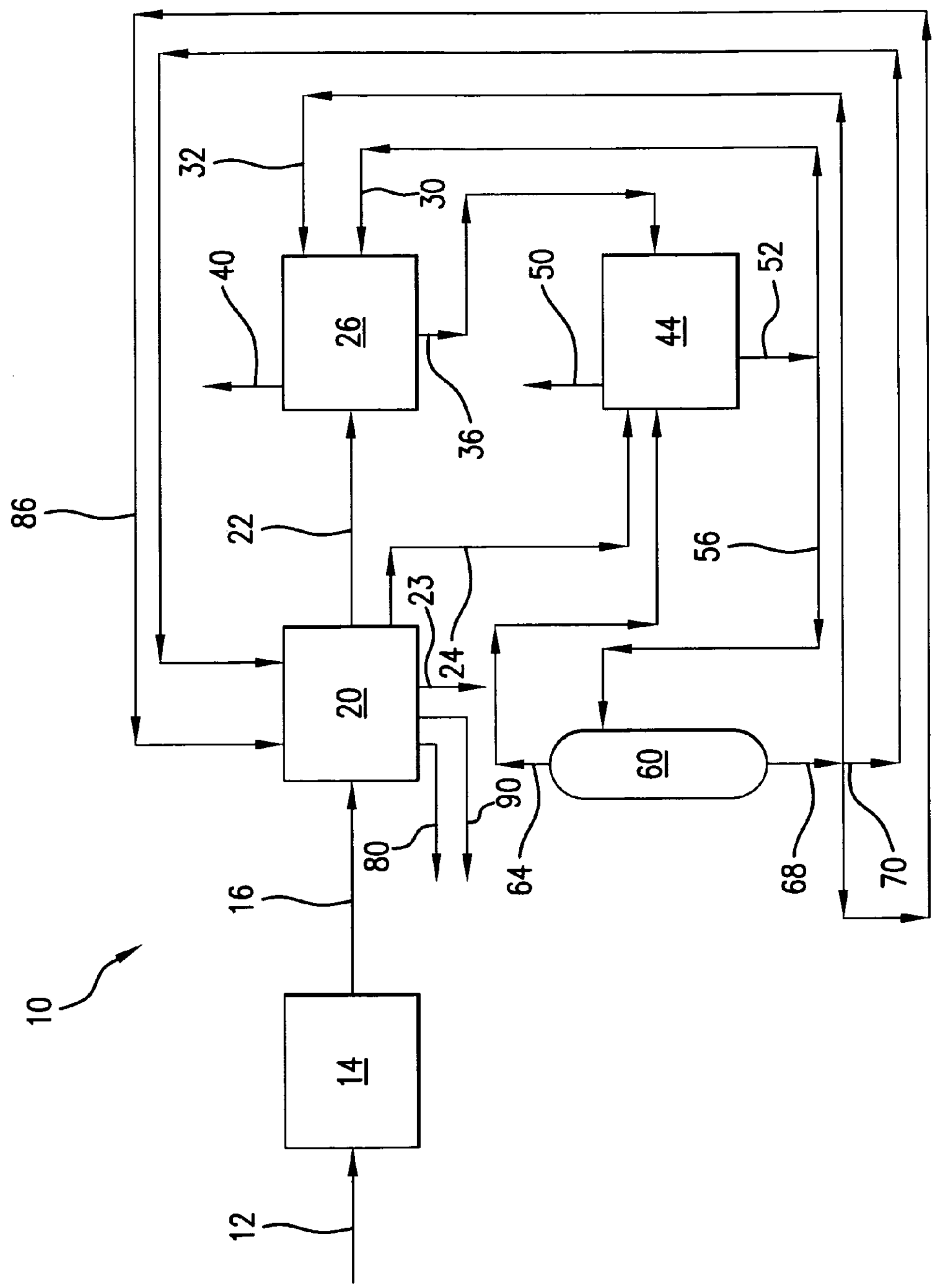
FIG. 1 is a simplified schematic diagram of an integrated oxygenate conversion and product recovery process in accordance with one preferred embodiment.

As will be appreciated, such processing may be embodied in a variety of processing arrangements. As representative, FIG. 1 illustrates a simplified schematic process flow diagram for a process scheme, generally designated by the reference numeral 10, for the conversion of oxygenates to olefins and utilizing a water-based recovery system employing a recycle water treatment process in accordance with one preferred embodiment.

More particularly, an oxygenate-containing feedstock or feedstream 12 such as generally composed of light oxygenates such as one or more of methanol, ethanol, dimethyl ether, diethyl ether, or mixtures thereof, is introduced into an oxygenate conversion zone or reactor section 14 wherein the oxygenate-containing feedstock contacts with an oxygenate conversion catalyst at reaction conditions effective to convert the oxygenate-containing feedstock to form an oxygenate conversion effluent stream comprising fuel gas hydrocarbons, light olefins, and $C_{4+}$ hydrocarbons, in a manner as is known in the art, such as, for example, utilizing a fluidized bed reactor.

As will be appreciated by those skilled in the art and guided by the teachings herein provided, such a feedstock may be commercial grade methanol, crude methanol or any combination thereof. Crude methanol may be an unrefined product from a methanol synthesis unit. Those skilled in that art and guided by the teachings herein provided will understand and appreciate that in the interest of factors such as improved catalyst stability, embodiments utilizing higher purity methanol feeds may be preferred. Thus, suitable feeds in such embodiments may comprise methanol or a methanol and water blend, with possible such feeds having a methanol content of between about 65% and about 100% by weight, preferably a methanol content of between about 80% and about 100% by weight and, in accordance one preferred embodiment, a methanol content of between about 95% and about 100% by weight.

A methanol-to-olefin unit feedstream may comprise between about 0 and about 35 wt-% and more preferably between about 5 and about 30 wt-% water. The methanol in the feedstream may comprise between about 70 and about 100 wt-% and more preferably between about 75 and about 95 wt-% of the feedstream. The ethanol in the feedstream may comprise between about 0.01 and about 0.5 wt-% and more typically between about 0.1 and about 0.2 wt-% of the feedstream although higher concentrations may be beneficial. When methanol is the primary component in the feedstream, the higher alcohols in the feedstream may comprise between about 200 and about 2000 wppm and more typically between about 500 and about 1500 wppm. Additionally, when methanol is the primary component in the feedstream, dimethyl ether in the feedstream may comprise between about 100 and about 20,000 wppm and more typically between about 200 and about 10,000 wppm.

The invention, however, also contemplates and encompasses embodiments wherein the oxygenate-containing feedstock is primarily dimethyl ether and, in certain embodiments, the oxygenate-containing feedstock is essentially dimethyl ether, either alone or with no more than insubstantial amounts of other oxygenate materials.

Reaction conditions for the conversion of oxygenates to light olefins are known to those skilled in the art. Preferably, in accordance with particular embodiments, reaction conditions comprise a temperature between about 200° and about 700° C., more preferably between about 300° and 600° C., and most preferably between about 400° and about 550° C. As will be appreciated by those skilled in the art and guided by the teachings herein provided, the reactions conditions are generally variable such as dependent on the desired products. For example, if increased ethylene production is desired, then operation at a reactor temperature between about 475° and about 550° C. and more preferably between about 500° and about 520° C., may be preferred. If increased propylene production is desired, then operation at a reactor temperature between about 350° and about 475° C. and more preferably between about 400° and about 430° C. may be preferred. The light olefins produced can have a ratio of ethylene to propylene of between about 0.5 and about 2.0 and preferably between about 0.75 and about 1.25. If a higher ratio of ethylene to propylene is desired, then the reaction temperature is generally desirably higher than if a lower ratio of ethylene to propylene is desired. In accordance with one preferred embodiment, a feed temperature range between about 120° and about 210° C. is preferred. In accordance with another preferred embodiment a feed temperature range of between about 180° and 210° C. is preferred. In accordance with one preferred embodiment, the temperature is desirably maintained below 210° C. to avoid or minimize thermal decomposition.

The oxygenate conversion reactor section 14 produces or results in an oxygenate conversion product or effluent stream 16 such as generally comprising hydrocarbon product materials such as fuel gas hydrocarbons, light olefins, and $C_{4+}$ hydrocarbons; by-product water; and remaining oxygenates such as methanol, dimethyl ether (DME) and other trace oxygenates including carbonyls such as acetaldehyde. The oxygenate conversion effluent stream 16 is passed to an effluent treatment zone 20 such as results in at least a compressed oxygenate conversion effluent vapor stream 22, an oxygenate conversion effluent liquid stream 23, a heavily laden water stream 80 containing heavy oxygenates and other heavy hydrocarbons, a relatively clean water stream 90 and a stream of circulated water 24. In practice, such a compressed oxygenate conversion effluent stream 22 may be the result of one or more compressor stages. Further, the stream of circulated water 24 may include water from one or more interstage condensations as well as water from various product recovery units or zones including, for example, wash water columns and the like.

The compressed oxygenate conversion effluent stream 22 or at least a portion thereof, is introduced into an oxygenate absorber zone 26, such as in the form of at least one absorber column. In the oxygenate absorber zone 26, oxygenates such as methanol, dimethyl ether (DME) and other trace oxygenates including carbonyls such as acetaldehyde are absorbed in circulated water, such as provided by the streams 30 and 32, described in greater detail below, and thus are separated from the hydrocarbon product materials.

Thus, the absorber zone 26 forms or results in an oxygenate-rich water stream 36 such as comprises such oxygenate materials in water and a stream 40 such as comprises such hydrocarbon product materials. The hydrocarbon product material stream 40, if desired and as described above, can be further processed such as by being conventionally washed with a caustic solution to neutralize any acid gases and dried prior to passage on to a desired gas concentration and product recovery system. Gas concentration and product recovery systems such as used for the processing of the effluent resulting from such oxygenate conversion processing are well known to those skilled in the art and do not generally form limitations on the broader practice of the invention as those skilled in the art and guided by the teachings herein provided will appreciate.

The oxygenate-rich water stream 36 is passed to an oxygenate stripper zone 44, such as in the form of at least one stripper column and such as includes a selected number stages such as in the form of trays or packing. In the oxygenate stripper zone 44, at least a portion of oxygenate species such as dimethyl ether and methanol, for example, can be stripped or otherwise effectively removed from the water such as to form an oxygenate-containing overhead stream 50, such as can be ultimately returned to the oxygenate conversion zone or reactor section 14 for further reaction processing, and a recycle water stream 52.

In practice, dimethyl ether is typically one of if not the most volatile oxygenate materials present in such an oxygenate-rich water stream. Consequently, the stripping requirement is minimal for DME removal alone from the circulated water. Methanol is less volatile than DME and, depending on the extent that the circulating water is stripped in the oxygenate stripper zone, the methanol level will build-up in the circulated water. Acetaldehyde is an example of a carbonyl form of trace oxygenate such as may be present in such an oxygenate conversion effluent stream. Those skilled in the art and guided by the teaching herein provided will appreciate that acetaldehyde could be expected to cause fouling in a caustic scrubber such as may desirably be downstream of an oxygenate absorber, as described above.

In accordance with one preferred embodiment, the oxygenate stripper zone 44 is operated in a manner, such as through the inclusion of additional trays or packing, such that carbonyls and, in particular, acetaldehyde, are/is more completely stripped such that the recycle water stream 52 desirably contains less than 150 mol ppm of carbonyls and acetaldehyde. In accordance with one preferred embodiment, the water is desirably treated to contain less than 80 mol ppm of carbonyls and acetaldehyde. In accordance with an alternative preferred embodiment, the water is treated to desirably contain less than 30 mol ppm of carbonyls and acetaldehyde. Additionally, and which could be a result of the lower concentration of carbonyls and, in particular, acetaldehyde, in the recycle water stream 52, the hydrocarbon product material stream 40 desirably contains less than 110 mol ppm of carbonyls and acetaldehyde. In accordance with one preferred embodiment, the hydrocarbon is desirably treated to contain less than 50 mol ppm of carbonyls and acetaldehyde. In accordance with an alternative preferred embodiment, the hydrocarbon is treated to desirably contain less than 20 mol ppm of carbonyls and acetaldehyde.

The water of recycle water stream 52 may subsequently be appropriately utilized in the associated process scheme as may be desired. For example, as shown for the process scheme 10 in FIG. 1, a portion of the recycle water stream, designated by the reference numeral 30, is returned to the oxygenate absorber zone 26 for contact with the compressed oxygenate conversion effluent stream 22, such as described above.

Another portion of the recycle water stream, designated by the reference numeral 56, is passed to a wash water stripper 60. In the wash water stripper 60, methanol and remaining oxygenates are effectively removed so as to produce an overhead stream 64 containing the recovered oxygenates and such as can be returned to the oxygenate stripper zone 44. The wash water stripper 60 also produces a bottoms water stream 68 containing insignificant amounts of dissolved oxygenates. A portion of the bottoms stream, designated by the reference numeral 70 and such as containing undesirable materials, can be returned to the effluent treatment zone 20 in which it is further processed for use in the treatment zone 20 and portions of which are removed from the process in water streams 80 and 90, such as in a manner known in the art. Another portion of the bottoms water stream, i.e., the above-referred to circulated water stream 32, can desirably be introduced into the oxygenate absorber zone 26, as described above, for the purpose of recovering additional oxygenates beyond the limitations imposed by the oxygenate content of the stream 30. An additional portion of the bottoms water stream 68, designated by the reference numeral 86, may be utilized to wash and recover methanol and other oxygenates from the liquid products formed in the zone 20, and ultimately recycled back to the zone 44 via the stream 24.

In a further embodiment of FIG. 1, the wash water stripper 60 may be omitted. In such a case, the recycle water stream 56 would be recycled to the effluent treatment zone for use therein and portions of which are removed from the process in water streams 80 and 90. A return stream (not shown) would be taken from water stream 90. An absorbent stream (not shown) from such a return stream would supplant circulated water stream 32 to the oxygenate absorber 26 and the remainder of the return stream would supplant stream 86 to the effluent treatment zone 20. As discussed above, the stripping requirement for DME removal from the circulated water is minimal. Methanol, although less volatile than DME, can be effectively stripped from the circulating water as the circulating water is stripped in the oxygenate stripper zone. Acetaldehyde, however, is an example of a carbonyl form of trace oxygenate such as may be present in such an oxygenate conversion effluent stream and such as may not be effectively stripped therefrom without the application of a more stringent than otherwise desired stripping regime.

To assist in carbonyl and, in particular, acetaldehyde recovery or removal, and as an alternative or supplement to stripping regime required in the above-described process scheme 10, another aspect of the invention involves treatment of a recycle or circulated water stream with a sulfite-containing material in order to form a treated water stream with an appropriately reduced or minimized carbonyl and, in particular, acetaldehyde content.

Figure 2:
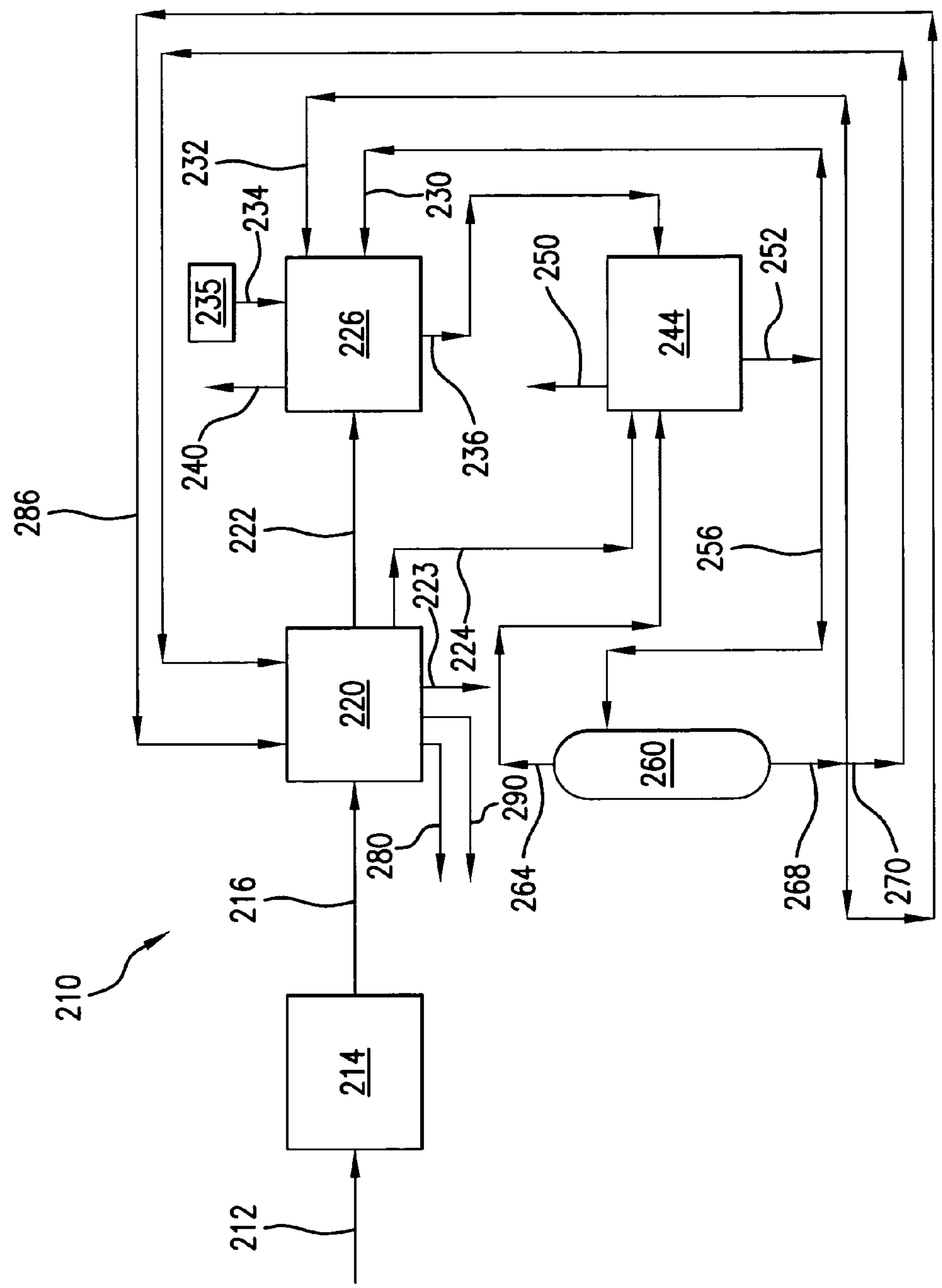
FIG. 2 is a simplified schematic diagram of an integrated oxygenate conversion and product recovery process in accordance with another preferred embodiment.

Turning now to FIG. 2, there is illustrated a simplified schematic process flow diagram for a process scheme, generally designated by the reference numeral 210, for the conversion of oxygenates to olefins and utilizing a water-based recovery system employing a recycle water treatment process in accordance with another preferred embodiment and such as employs treatment of a recycle or circulated water stream with a sulfite-containing material in order to form a treated water stream with an appropriately reduced or minimized carbonyl and, in particular, acetaldehyde content.

The process scheme 210 is generally similar to the process scheme 10 described above and having an oxygenate-containing feedstock or feedstream 212, such as described above, that is introduced into an oxygenate conversion zone or reactor section 214 wherein the oxygenate-containing feedstock contacts with an oxygenate conversion catalyst at reaction conditions effective to convert the oxygenate-containing feedstock and to form an oxygenate conversion effluent stream comprising fuel gas hydrocarbons, light olefins, and $C_{4+}$ hydrocarbons, in a manner as is known in the art, such as, for example, utilizing a fluidized bed reactor.

As described above, the oxygenate conversion reactor section 214 produces or results in an oxygenate conversion product or effluent stream 216 such as generally comprising hydrocarbon product materials such as fuel gas hydrocarbons, light olefins, and $C_{4+}$ hydrocarbons; by-product water; and remaining oxygenates such as methanol, dimethyl ether (DME) and other trace oxygenates including carbonyls such as acetaldehyde. The oxygenate conversion effluent stream 216 is passed to an effluent treatment zone 220 such as results in at least a compressed oxygenate conversion effluent vapor stream 222, an oxygenate conversion effluent liquid stream 223, a heavily laden water stream 280 containing heavy oxygenates and other heavy hydrocarbons, a relatively clean water stream 290 and a stream of circulated water 224.

The compressed oxygenate conversion effluent stream 222 or at least a portion thereof, is introduced into an oxygenate absorber zone 226, such as in the form of at least one absorber column. As in the above-described embodiment, in the oxygenate absorber zone 226, oxygenates such as methanol, dimethyl ether (DME) and other trace oxygenates including carbonyls such as acetaldehyde can be absorbed in circulated water, such as provided by the streams 230 and 232, described in greater detail below, and thus are separated from the hydrocarbon product materials.

To assist in carbonyl and, in particular, acetaldehyde recovery or removal, and as an alternative or supplement to stripping regime required in the above-described process scheme 10, the process scheme 210 treats the recycle or circulated water stream with a sulfite-containing material in order to form a treated water stream with an appropriately reduced or minimized carbonyl and, in particular, acetaldehyde content. The effective treatment of a water stream with such a sulfite-containing material in accordance with one preferred embodiment can be realized by treating the water stream with a solution of a sulfite compound comprising an alkali metal or an alkaline earth metal cation. Examples of suitable such cation materials include sodium, potassium, magnesium and calcium.

As used herein, references to a "sulfite-containing material" are to be understood to include sulfite compounds, bisulfite compounds and mixtures thereof. Sodium bisulfite is an example of one preferred "sulfite-containing material" for use in practice of such aspect of the invention.

In the process scheme 210, such a sulfite-containing material is added to the oxygenate absorber zone 226 as shown by the stream 234 from the sulfite-containing material reservoir, designated by the reference numeral 235. Such addition of a sulfite-containing material may also include or involve a pH adjustment of the oxygenate absorber zone 226 such as to desirably maintain the pH of the aqueous solution in the absorber between pH 1 and 10, more preferably between pH 2 and 8, and, most preferably, between pH 4 to 7.

As described above, the oxygenate absorber zone 226 forms or results in an oxygenate-rich water stream 236 such as comprises such oxygenate materials in water and a stream 240 such as comprises such hydrocarbon product materials. The hydrocarbon product material stream 240, if desired and as described above, can be further processed such as by being conventionally washed with a caustic solution to neutralize any acid gases and dried prior to passage on to a desired gas concentration and product recovery system. Gas concentration and product recovery systems such as used for the processing of the effluent resulting from such oxygenate conversion processing are well known to those skilled in the art and do not generally form limitations on the broader practice of the invention as those skilled in the art and guided by the teachings herein provided will appreciate.

The oxygenate-rich water stream 236, containing unreacted sulfite and bisulfite addition compounds, is passed to an oxygenate stripper zone 244, such as in the form of at least one stripper column and such as includes a selected number stages such as in the form of trays or packing. In the oxygenate stripper zone 244, at least a portion of oxygenate species such as dimethyl ether and methanol, for example, can be stripped or otherwise effectively removed from the water such as to form an oxygenate-containing overhead stream 250, such as can be ultimately returned to the oxygenate conversion zone or reactor section 214 for further reaction processing and a recycle water stream 252. The unreacted sulfite and bisulfite addition compounds are sufficiently nonvolatile so as to preferentially remain in the recycle water stream 252. The stream 250 may potentially contain oxygenates such as from the decomposition of bisulfite addition compounds and entrained bisulfite addition compounds.

The water of the recycle water stream 252 may subsequently be appropriately utilized in the associated process scheme as may be desired. For example, as shown for the process scheme 210 in FIG. 2, a portion of the recycle water stream, designated by the reference numeral 230, is returned to the oxygenate absorber zone 226 for contact with the compressed oxygenate conversion effluent stream 222, such as described above.

Another portion of the recycle water stream, designated by the reference numeral 256, is passed to a wash water stripper 260. In the wash water stripper 260, methanol and remaining oxygenates are effectively removed so as to produce a bottoms water stream 268 containing insignificant amounts of dissolved oxygenates, and an overhead stream 264 containing the recovered oxygenates, such as can be returned to the oxygenate stripper zone 244. The unreacted sulfite and bisulfite addition compounds are sufficiently nonvolatile so as to preferentially remain in the recycle water stream 268.

As described above, a portion of the bottoms stream, designated by the reference numeral 270 and such as containing undesirable materials, can be returned to the effluent treatment zone 220 and further processed therein with portions of which are removed from the process in water streams 280 and 290, such as in a manner known in the art. Another portion of the bottoms stream, i.e., the above-referred to circulated water stream 232, can desirably be introduced into the oxygenate absorber zone 226, as described above for the purpose of recovering additional oxygenates beyond the limitations imposed by the oxygenate content of stream 230. Yet another portion of the stream 268, designated by the reference numeral 286, may be utilized to wash and recover methanol and other oxygenates from the liquid products formed in the effluent treatment zone 220, and ultimately recycled back to the oxygenate stripper zone 244 via the stream 224. The presence of unreacted sulfite in the stream 268 may be beneficial for recovery of additional acetaldehyde and other carbonyls in the effluent treatment zone 220 and the oxygenate absorber zone 226.

In accordance with such embodiment, and as an alternative or supplement to stripping regime required in the above-described process scheme 10, desired carbonyl and, in particular, acetaldehyde, recovery or removal, is realized such that recycle or circulated water stream is treated with a sulfite-containing material to form a treated water stream desirably containing less than 150 mol ppm of carbonyls and acetaldehyde. In accordance with one preferred embodiment, the water is desirably treated with a sulfite-containing material to form a treated water stream containing less than 80 mol ppm of carbonyls and acetaldehyde. In accordance with an alternative preferred embodiment, the water is desirably treated with a sulfite-containing material to form a treated water stream containing less than 30 mol ppm of carbonyls and acetaldehyde. Additionally, and which could be a result of the lower concentration of carbonyls and, in particular, acetaldehyde, in the recycle water stream 252, the hydrocarbon product material stream 240 desirably contains less than 110 mol ppm of carbonyls and acetaldehyde. In accordance with one preferred embodiment, the hydrocarbon is desirably treated to contain less than 50 mol ppm of carbonyls and acetaldehyde. In accordance with an alternative preferred embodiment, the hydrocarbon is treated to desirably contain less than 20 mol ppm of carbonyls and acetaldehyde.

It should be noted in the foregoing, that the oxygenate strippers, i.e., 44 and 244, and the wash water strippers, i.e., 60 and 260, may be equipped with reboilers, while neither of the strippers 44, 60, 244, 260 or the absorbers 26, 226 are equipped with a condenser. However, coolers may be provided at least on lines 86, 286 and 56, 256.

While such aspect of the invention has been described making specific reference to an embodiment wherein the sulfite-containing material is added to the recycle or circulated water by way of addition to the oxygenate absorber zone, those skilled in the art and guided by the teachings herein provided will appreciate that the broader practice of such aspect is not necessarily so limited. For example, the invention can be practiced employing various alternative location or sites for the addition of a desired sulfite-containing material. Examples of such alternative sulfite-containing material addition locations include any combination of the following locations and streams: the effluent treatment zone 220, the oxygenate stripper zone 244, the wash water stripper 260 and the various above-described water-containing streams 224, 230, 232, 236, 252, 256, and 268.

Thus, through the appropriate treatment of the process water, such as via either or both the application of a more stringent oxygenate stripping regime and the introduction of an appropriate sulfite-containing material, there are provided processing schemes and arrangements for the conversion of an oxygenate-containing feedstock to olefins, particularly light olefins and which processing is desirably effective and efficient for the removal or recovery of carbonyls, particularly acetaldehyde, such as to improve or facilitate downstream processing.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

EXAMPLE

The flow scheme of FIG. 1 of the present invention is simulated to illustrate the attainment of a recycle water stream with the desired concentration of carbonyls which in this case is acetaldehyde. A compressed MTO olefinic vapor product stream 22 containing oxygenates including 660 mol-ppm acetaldehyde is introduced to a bottom of an oxygenate absorber 26 at 38° C. Hydrocarbon products are removed from the overhead 40 at 40° C. and 19 bar (gauge) to be treated in a downstream caustic scrubber for removing acid gases. An oxygenate-rich water stream 36 exits the bottoms of the oxygenate absorber at 40° C. The oxygenate water stream 36 is introduced to an oxygenate stripper 44 with a reboiler at a tray that is the $16^{th}$ tray from the top. An oxygenate stream 50 is recovered in the overhead for recycling to an oxygenate conversion reactor 14. A portion of recycle water stream 52 at 137° C. from the bottoms of the oxygenate stripper 44 is cooled and recycled to the oxygenate absorber 26 at 40° C. and 26 trays above the bottom. As shown in FIG. 1, additional water is added to the top trays in the oxygenate absorber 26 and the oxygenate stripper 44. The vapor to liquid molar ratio in the oxygenate absorber was kept nearly constant at 0.14 and the energy input to the oxygenate stripper reboiler was kept nearly constant at 0.77 kW/kgmol of oxygenate water stream 36 while the number of trays disposed below the feed tray in the oxygenate stripper 44 were varied.

| No. of Trays between feed and bottoms | 5 | 15 | 25 |
|---|---|---|---|
| Acetaldehyde concentration in water stream 36 (mol-ppm) | 147 | 34 | 21 |
| Acetaldehyde concentration in hydrocarbon stream 40 (mol-ppm) | 102 | 23 | 14 |

When twenty-five trays are disposed below the feed tray in the oxygenate the acetaldehyde concentration in the recycle water is 21 mol ppm and the bon product stream from the overhead of the oxygenate absorber is 14 mol ppm well within the desirable level of less than 20 mol ppm.

What is claimed is:

1. A process for producing light olefins from an oxygenate-containing feedstock, said process comprising:

contacting the oxygenate-containing feedstock in an oxygenate conversion reactor with an oxygenate conversion catalyst and at reaction conditions effective to convert the oxygenate-containing feedstock to form an oxygenate conversion effluent stream comprising fuel gas hydrocarbons, light olefins, $C_{4+}$ hydrocarbons and remaining oxygenate materials including a quantity of carbonyls;

absorbing at least a portion of the remaining oxygenate material from the effluent stream in a vapor-liquid adsorber, including at least a portion of the quantity of carbonyls, in a quantity of water to form an oxygenate-rich water process stream, and a hydrocarbon product stream having less than 110 mol ppm of carbonyls and acetaldehyde; and stripping oxygenate material from the oxygenate-rich water process stream to form a recycle water stream;

with at least a portion of the recycle water stream water forming said quantity of water used to absorb at least a portion of the remaining oxygenate material and said process additionally comprising said quantity of water having been treated to contain less than 150 mol ppm of carbonyls wherein said quantity of water having been treated to contain less than 150 mol ppm of carbonyls comprises said stripping of oxygenate material from the oxygenate-rich water process stream being performed at stripping conditions whereby the recycle water stream contains less than 150 mol ppm of carbonyls.

2. The process of claim 1 wherein said quantity of water has been treated to contain less than 80 mol ppm of carbonyls.

3. The process of claim 1 wherein said quantity of water has been treated to contain less than 30 mol ppm of carbonyls.

4. The process of claim 1 wherein said quantity of water having been treated to contain less than 150 mol ppm of carbonyls comprises treating the recycle water stream with a sulfite-containing material to form a treated recycle water stream containing no more than 150 mol ppm carbonyls.

5. The process of claim 4 wherein said treating of the recycle water stream with sulfite-containing material comprises treating the recycle water stream with a solution of a sulfite compound comprising an alkali metal or an alkaline earth metal cation.

6. The process of claim 5 wherein the sulfite compound comprises sodium cation.

7. The process of claim 5 wherein the sulfite compound comprises potassium cation.

8. The process of claim 1 wherein the oxygenate-containing feedstock comprises an oxygenate-containing feedstock material selected from the group consisting of methanol, dimethyl ether and combinations thereof.

9. The process of claim 1 wherein the oxygenate-containing feedstock comprises the carbonyl acetaldehyde.

10. A process for producing light olefins from an oxygenate-containing feedstock, said process comprising:

contacting the oxygenate-containing feedstock in an oxygenate conversion reactor with an oxygenate conversion catalyst and at reaction conditions effective to convert the oxygenate-containing feedstock to form an oxygenate conversion effluent stream comprising fuel gas hydrocarbons, light olefins, $C_{4+}$ hydrocarbons and remaining oxygenate materials including a quantity of acetaldehyde;

absorbing at least a portion of the remaining oxygenate material from the effluent stream in a vapor-liquid adsorber, including at least a portion of the quantity of acetaldehyde, in a quantity of water to form an oxygenate-rich water process stream and a stream of hydrocarbon product; and stripping oxygenate material from the oxygenate-rich water process stream to form a recycle water stream;

with at least a portion of the recycle water stream water forming said quantity of water used to absorb at least a portion of the remaining oxygenate material and said process additionally comprising said hydrocarbon product having been treated to contain less than 110 mol ppm of acetaldehyde.

11. The process of claim 10 wherein said hydrocarbon product has been treated to contain less than 50 mol ppm of acetaldehyde.

12. The process of claim 10 wherein said hydrocarbon product has been treated to contain less than 20 mol ppm of acetaldehyde.

13. The process of claim 10 comprising said stripping of oxygenate material from the oxygenate-rich water process stream being performed at stripping conditions whereby the recycle water stream contains less than 150 mol ppm of acetaldehyde.

14. The process of claim 10 comprising treating the recycle water stream with a sulfite-containing material to form a treated recycle water stream containing no more than 150 mol ppm acetaldehyde.

15. The process of claim 14 wherein the sulfite compound is sodium bisulfite.

* * * * *